(12) United States Patent
Makoto et al.

(10) Patent No.: US 8,668,813 B2
(45) Date of Patent: Mar. 11, 2014

(54) PLASMA GENERATION METHOD AND APPARATUS

(71) Applicant: Samsung Electronics Co., Ltd, Suwon (JP)

(72) Inventors: Miyamoto Makoto, Kanagawa (JP); Nakayama Yoko, Kanagawa (JP); Kumagai Yuuki, Kanagawa (JP); Takenoshita Kazutoshi, Kanagawa (JP)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/797,201

(22) Filed: Mar. 12, 2013

(65) Prior Publication Data

US 2013/0189154 A1    Jul. 25, 2013

Related U.S. Application Data

(62) Division of application No. 13/312,253, filed on Dec. 6, 2011, now Pat. No. 8,425,853.

(30) Foreign Application Priority Data

Dec. 8, 2010   (JP) ................................. 2010-273450

(51) Int. Cl.
*B01J 19/08*       (2006.01)

(52) U.S. Cl.
USPC ........................................................ 204/164

(58) Field of Classification Search
USPC ........................................................ 204/164
See application file for complete search history.

(56) References Cited

FOREIGN PATENT DOCUMENTS

| DE | 6813442 | 6/1969 |
|---|---|---|
| EP | 2128550 | 12/2009 |
| FR | 1341414 | 12/1962 |
| FR | 2564335 | 11/1985 |
| JP | 2005-224757 | 8/2005 |
| JP | 2009-255027 | 11/2009 |
| KR | 10-2005-0080435 | 8/2005 |
| KR | 10-2006-0124864 | 12/2006 |
| KR | 10-2011-0024708 | 3/2011 |
| WO | 02/35576 | 5/2002 |

OTHER PUBLICATIONS

Extended European Search Report issued Sep. 12, 2012 in corresponding European Patent Application No. 11191817.3.
Office Action for co-pending U.S. Appl. No. 13/312,253, dated Sep. 20, 2012.
Notice of Allowance for co-pending U.S. Appl. No. 13/312,253 dated Dec. 12, 2012.
U.S. Appl. No. 13/312,253, filed Dec. 6, 2011, Miyamoto Makoto et al., Samsung Electronics Co., Ltd.
Partial European Search Report dated Mar. 28, 2012 issued in corresponding European Patent Application No. 11191817.3.

*Primary Examiner* — Kishor Mayekar
(74) *Attorney, Agent, or Firm* — Staas & Halsey LLP

(57) ABSTRACT

A plasma generation apparatus and method, which achieve both sterilization and deodorization of attached bacteria even under the condition that steam or fine droplets of water are present. A pair of electrodes is prepared, plasma discharge is carried out by applying designated voltage between the pair of electrodes, fluid passage holes are provided at corresponding parts of respective electrodes so as to communicate with each other, and steam or fine droplets of water are applied to the fluid passage holes and plasma generated around the fluid passage holes.

7 Claims, 16 Drawing Sheets

FIG. 11
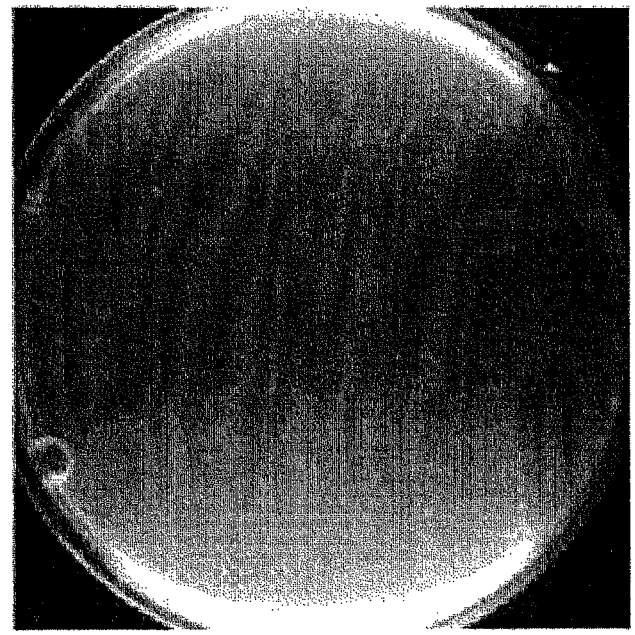
OPERATION OF PLASMA GENERATION APPARATUS
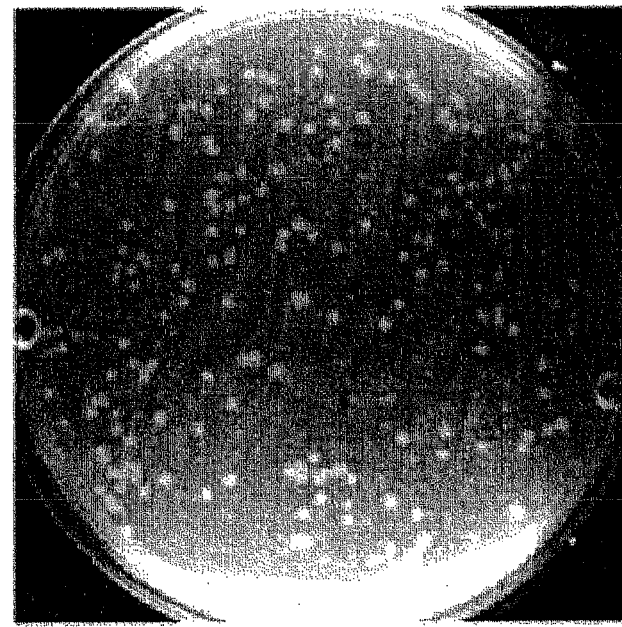
NON-OPERATION OF PLASMA GENERATION APPARATUS

PLASMA GENERATION METHOD AND APPARATUS

CROSS-REFERENCE TO RELATED APPLICATIONS

This application is a divisional application of U.S. application Ser. No. 13/312,253, filed Dec. 6, 2011, which claims the priority benefit of Japanese Patent Application No. 2010-273450, filed on Dec. 8, 2010 in the Japanese Patent Office, the disclosures of each of which are incorporated herein by reference.

BACKGROUND

1. Field

Example embodiments of the following description relate to a plasma generation method and apparatus, and more specifically, to a method and apparatus for sterilization and deodorization of attached bacteria under the condition that steam or fine droplets of water are present.

2. Description of the Related Art

Recently, the requirements of air quality control in living environments, such as, sterilization or deodorization, have become more stringent due to the increase in individuals suffering from atopy, asthma, and allergies, or the increase in the risk of infectious diseases, represented by the explosive spread of new types of influenza. Further, as society becomes increasingly affluent, the amount of storage food increases or an opportunity to store leftovers increases, and thus, the importance of controlling an environment in the storage equipment, such as a refrigerator, increases.

In order to control air quality in living environments, physical control generally using a filter was conventionally executed. Through physical control, relatively large dust floating in air and/or bacteria or viruses may be trapped according to sizes of filter holes. Further, activated carbon having anhydrous absorption sites may trap odorous molecules. However, since, in order to trap such substances, air in a space of a target object to be controlled needs to completely pass through the filter, the size of the apparatus must be large, the maintenance cost required to replace the filter is increased, and the apparatus has no effect upon attached particles. Therefore, in order to achieve sterilization and deodorization of the attached particles, chemical active species may be discharged to a space desired to be sterilized or deodorized. When a medicine is distributed, or an aromatic or a deodorizer is discharged, active species need to be prepared in advance and periodic supplement of the active species is indispensable. On the other hand, units which generate plasma in the atmosphere and attempt sterilization and deodorization, using chemically active species generated, due to plasma generation, have recently been increasingly proposed.

Technology for generating plasma in the atmosphere through discharge and achieving sterilization and deodorization by ions or radicals (hereinafter, referred to as active species) generated thereby, may be classified into two types, described below.

(1) A passive plasma generation apparatus, which causes bacteria or viruses floating within the atmosphere (hereinafter, referred to as floating bacteria) or odorous materials (hereinafter, referred to as odors) to react with active species within a restricted volume in the apparatus (for example, Japanese Patent Laid-open Publication No. 2002-224211); and (2) An active plasma generation apparatus, which discharges active species generated by a plasma generation unit into a closed space (for example, a living room, a bath room, the inside of a car, etc) having a larger volume than the passive plasma generation apparatus, and causes the discharged active species to react with floating bacteria or odors due to collision with the floating bacteria or odors in the atmosphere (for example, Japanese Patent Laid-open Publication No. 2003-79714).

The passive plasma generation apparatus may be advantageous in that high sterilization and deodorization of the air is expected through generation of active species of a high concentration due to generation of plasma in a small volume. However, the passive plasma generation apparatus may be disadvantageous in that the floating bacteria or odors need to be introduced into the apparatus, and thus, the size of the apparatus is increased, ozone as a byproduct due to plasma generation is generated, and separate installation of a filter to absorb or decompose ozone to prevent ozone from leaking to the outside of the apparatus is required.

In addition, the active plasma generation apparatus may be advantageous in that the size of the apparatus is relatively reduced, and sterilization of bacteria attached to the surfaces of clothes or household goods (hereinafter, referred to as attached bacteria), or decomposition of odors absorbed to the surfaces, is expected in addition to sterilization of floating bacteria or decomposition of odors in air. However, the active plasma generation apparatus may be disadvantageous in that the concentration of active species is decreased due to diffusion of the active species into a considerably large closed space, as compared with the volume of the apparatus, and thus, sterilization and deodorization are expected only upon active species having a long life. Consequently, deodorization effects are scarcely expected in a space having a high concentration of odors (concentration 10,000 times greater than the concentration of the active species).

As described above, the passive plasma generation apparatus exhibits effects restricted to floating bacteria or odors contained in an air flow introduced into the apparatus, and the active plasma generation apparatus exhibits effects upon floating bacteria, attached bacteria, and odors having a low concentration. Further, conventional plasma generation apparatuses may be disadvantageous in that an amount of generated ions or radicals is reduced due to lowering of the performance of the plasma generation apparatus in a high-humidity state. That is, the conventional plasma generation apparatuses may achieve either sterilization of floating bacteria and deodorization in a high-humidity state, or sterilization of floating bacteria and attached bacteria having a low concentration and deodorization of attached odors having a low concentration in a high-humidity state.

However, there are several situations in daily life in which both sterilization of attached bacteria and deodorization of odors of a high concentration are desired to be simultaneously achieved under the condition that steam or fine droplets of water are present in a high-humidity environment. Typically, there are home appliances for treating water. For example, a washing machine is generally in a high humidity state, various attached bacteria are present on the surface of a tub, and odors generated due to remaining water or decomposition of a detergent occur within the washing machine. Further, various bacteria or odors generated due to remaining food waste may be present within a dish washer.

SUMMARY

The foregoing and/or other aspects are achieved by providing a plasma generation apparatus and method, which achieve both sterilization and deodorization of attached bacteria, for example, under the condition that steam or fine droplets of water are present in a high-humidity environment, and particularly, a plasma generation apparatus and method which increase an amount of generated active species and exhibit both an active function of generating functional mist by interaction between the active species and steam or fine droplets of water to achieve deodorization and a passive function of discharging functional mist to the outside of the apparatus to sterilize attached bacteria.

The foregoing and/or other aspects are also achieved by providing a plasma generation method, in which a pair of electrodes is prepared and plasma discharge is carried out by applying designated voltage between the pair of electrodes, fluid passage holes are provided at corresponding parts of respective electrodes so as to communicate with each other, and steam or fine droplets of water are applied to the fluid passage holes and plasma generated around the fluid passage holes. In this case, the corresponding parts mean that the respective fluid holes formed on the electrodes are located at the same positions as seen from the plane directions of the electrodes, and are located at approximately the same x and y coordinate positions of the electrodes as the pair of electrodes on an x-y plane is observed in the z axis direction in a rectangular coordinate system.

Through the above configuration, an amount of plasma generated from the respective corresponding fluid passage holes may be increased and a contact area between the plasma and a fluid may be increased, thereby increasing an amount of generated active species. Further, a contact area between the plasma and the steam or fine droplets of water may be increased. The steam or fine droplets of water may contact the active species generated from the fluid passage holes, and thus, the active species may charge or be mixed with the steam or fine droplets of water, become functional mist, and be discharged to the outside. The functional mist discharged to the outside may sterilize flowing bacteria and attached bacteria. Moreover, the amount of the active species generated from plasma may be increased, thereby exhibiting a sufficient deodorizing function.

The foregoing and/or other aspects are also achieved by providing a plasma generation method, in which a pair of electrodes is prepared and plasma discharge is carried out by applying designated voltage between the pair of electrodes, wherein through holes are provided on one electrode such that openings of the through holes on an opposite surface of the electrode facing the other electrode are closed by the other electrode, and steam or fine droplets of water are applied to openings of the through holes on the other surface of the electrode and plasma generated around the through holes.

Through the above configuration, an amount of plasma generated from the respective corresponding fluid passage holes may be increased and a contact area between the plasma and a fluid may be increased, thereby increasing an amount of generated active species. Further, a contact area between the plasma and the steam or fine droplets of water may be increased. Thereby, an amount of generated functional mist may be increased, thus sterilizing flowing bacteria and attached bacteria. Moreover, the amount of the active species generated from plasma may be increased, thereby exhibiting a sufficient deodorizing function.

An embodiment of the present disclosure provides that the fine droplets of water may have a particle size of approximately 100 μm or less. The reason why the fine droplets of water have a particle size of approximately 100 μm or less is that a distance between the electrodes is approximately 100 μm or less, and thus, steam or fine droplets of water having a particle size of more than approximately 100 μm are not be applied to the electrodes. Further, droplets of water having a particle size exceeding approximately 100 μm form, for example, a water drop shape like rain, are not contained in a fluid, and fall by gravity, thus not generating functional mist.

In order to increase the number of the active species contained in the fluid having passed through the fluid passage holes to increase the amount of the generated functional mist and to suppress concentration of generated ozone, voltage in a pulse mode may be applied to the respective electrodes and may have a peak value within the range of approximately 100V to 5,000V and a pulse width in the range of approximately 0.1 μs to 300 μs.

Another embodiment provides that the steam or fine droplets of water may be supplied when a temperature of the pair of electrodes is more than a designated value. That is, if the temperature of the pair of electrodes is more than the designated value, it may be judged that an amount of moisture in the atmosphere and an amount of moisture attached to the electrodes is lowered, and thus, the steam or fine droplets of water may be supplied.

Further, the pair of electrodes may be heated by a heating unit when the temperature of the pair of electrodes is less than the designated value. Thereby, since it is judged that the amount of moisture attached to the electrodes is excessively large, the electrodes may be heated to evaporate the moisture attached to the electrodes, without supply of the steam or fine droplets of water. Accordingly, performance of the electrodes is not lowered due to moisture, and the steam or fine droplets of water may be applied to the fluid passage holes at all times.

The foregoing and/or other aspects are also achieved by providing a plasma generation apparatus, which includes a pair of electrodes provided with a dielectric film on at least one of opposite surfaces thereof, a voltage application unit to apply designated voltage between the pair of electrodes to carry out plasma discharge, and fluid passage holes provided at corresponding parts of respective electrodes so as to communicate with each other, a fluid contacting the plasma to generate ions or radicals when the fluid passes through the fluid passage holes, wherein a supply device to supply steam or fine droplets of water to the fluid passage holes or plasma generated around the fluid passage holes is provided.

In this case, since the dielectric film is provided on at least one electrode among the pair of electrodes, a gap to generate plasma may be formed between the respective electrodes without a spacer to form the gap.

In order to increase a contact area between a fluid passing through the fluid passage holes and the plasma in order to increase an amount of generated functional mist, at least parts of the outlines of the respective fluid passage holes, corresponding to each other, may be located at different positions as seen from the plane direction of the electrodes.

In order to locate the at least parts of the outlines of the respective fluid passage holes corresponding to each other at different positions, an opening size of the fluid passage holes formed on one electrode among the pair of electrodes may be smaller than an opening size of the fluid passage holes formed on the other electrode by approximately 10 μm or more. In addition, the fluid passage holes having the same opening size may be disposed such that the centers of the openings thereof do not match each other.

In order to increase an amount of discharged active species to achieve deodorization of the fluid passing through or having passed through the fluid passage holes, and sterilization of floating bacteria contained in the fluid to increase an amount of generated functional mist, through holes may be provided on one electrode separately from the fluid passage holes and openings of the through holes on an opposite surface of the electrode facing the other electrode may be closed by the other electrode. The fluid, after having passed through the fluid passage holes, and the steam or fine droplets of water may be introduced into the through holes to contact the plasma, or the fluid prior to passing through the fluid passage holes and the steam or fine droplets of water may be introduced into the through holes to contact the plasma, thereby remarkably improving effects of the plasma generation apparatus.

An example embodiment provides that an opening size of the through holes may be smaller than the opening size of the fluid passage holes by approximately 10 μm or more.

Another example embodiment provides that the dielectric film may have a surface roughness of more than approximately 0.1 μm and less than 100 μm. Thereby, even if the pair of electrodes is stacked without use of a spacer, a space in which the plasma is generated may be formed by the surface roughness.

In order to allow the fluid to effectively pass through the fluid passage holes to promote generation of active species and to increase deodorizing effect, the plasma generation apparatus may further include an air blowing device to forcibly blow air toward the fluid passage holes.

Another example embodiment provides that a flow velocity of air blown by the air blowing device and passing through the fluid passage holes may be in the range of approximately 0.1 m/s to 10 m/s. When the flow velocity of air is less than approximately 0.1 m/s, efficiency of the fluid passing through the fluid passage holes is low, and when the flow velocity of air is less than approximately 10 m/s, reaction between the fluid and the plasma is sufficiently carried out.

In order to prevent lowering of performance of the pair of electrodes due to moisture, a water repellent property may be imparted to the opposite surface of at least one electrode, among the pair of electrodes, so that a contact angle of water drops with the opposite surface is more than 90 degrees. In order to uniformly maintain applied voltage to keep a large amount of generated active species, even if an excessive amount of moisture contacts the plasma electrode unit, the opposite surfaces of the electrodes have the water repellent property.

If a conventional plasma generation apparatus requiring high voltage is applied to a refrigerator using a combustible gas instead of Freon gas, safety may be lowered. The used combustible gas may leak in the refrigerator, and sparks causing high voltage which are generated in the above atmosphere may ignite and cause an explosion accident. Therefore, the plasma generation apparatus may further include an explosion proof device, including protective covers disposed at the outside of the pair of the electrodes to prevent flame generated from the combustible gas introduced into the fluid passage holes by the plasma from propagating to the outside over the protective covers.

In order to obtain safety without lowering deodorizing and sterilizing capacities, each of the protective covers may include a metal mesh disposed at the outside of the pair of the electrodes, and the metal mesh may have a wire diameter of approximately 1.5 mm or less and an aperture ratio of approximately 30% or more.

Additional aspects, features, and/or advantages of example embodiments will be set forth in part in the description which follows and, in part, will be apparent from the description, or may be learned by practice of the disclosure.

BRIEF DESCRIPTION OF THE DRAWINGS

These and/or other aspects of the present disclosure will become apparent and more readily appreciated from the following description of the embodiments, taken in conjunction with the accompanying drawings of which:

FIG. 11 represents photographs illustrating results of a sterilization test of colon bacilli;

DETAILED DESCRIPTION

Figure 1:
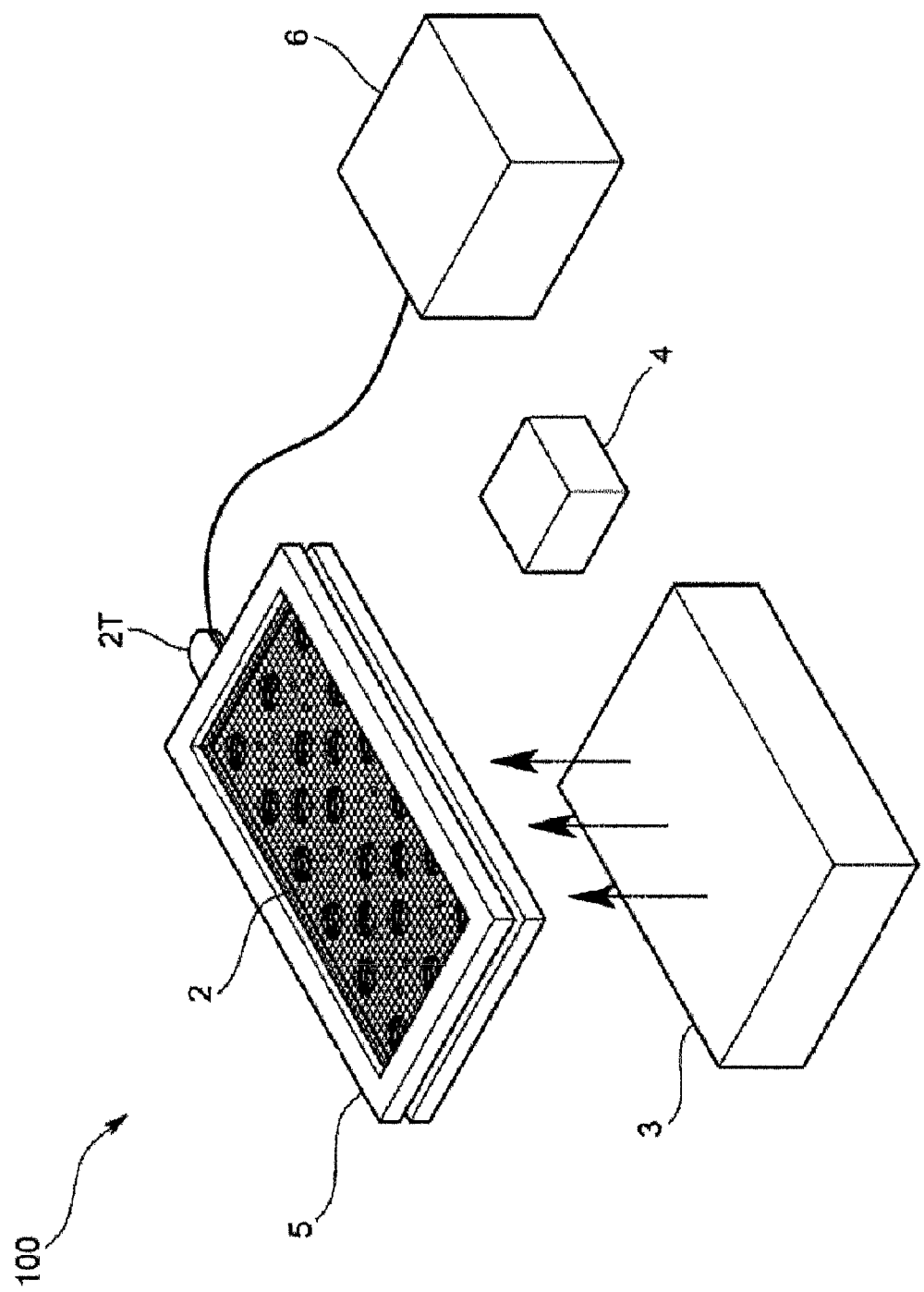
FIG. 1 is a perspective view illustrating a plasma generation apparatus in accordance with example embodiments.

Reference will now be made in detail to the example embodiments of the present disclosure, examples of which are illustrated in the accompanying drawings, wherein like reference numerals refer to like elements throughout.

A plasma generation apparatus 100 in accordance with an example embodiment of the present disclosure is used in a home appliance, for example, a refrigerator, a washing machine, a laundry dryer, a cleaner, an air conditioner or an air cleaner, particularly, even in a high-humidity environment, and is employed as a sterilization and deodorization apparatus, which achieves deodorization of air at the inside or outside of the home appliance, or sterilization of floating bacteria or attached bacteria at the inside or outside of the home appliance.

Figure 2:
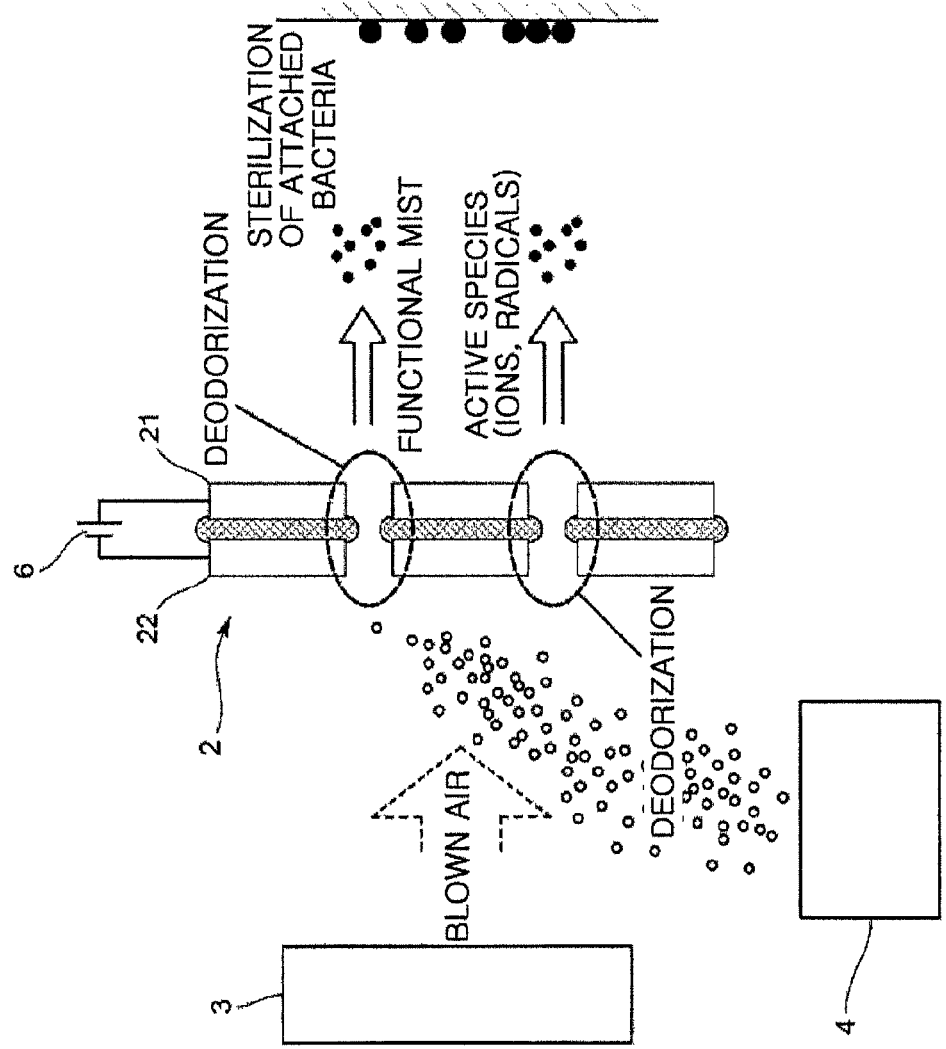
FIG. 2 is a schematic view illustrating operation of the plasma generation apparatus, according to example embodiments.

In more detail, as shown in FIGS. 1 and 2, the plasma generation apparatus 100 includes a plasma electrode unit 2 to generate active species, such as ions or radicals, through micro gap plasma, an air blowing device 3 provided at the outside of the plasma electrode unit 2 to forcibly blow air (an air current) to the plasma electrode unit 2, a fine droplet supply device 4 to supply fine droplets of water (mist) to the plasma electrode unit 2, an explosion proof device 5 provided at the outside of the plasma electrode unit 2 to prevent flame generated by the plasma electrode unit 2 from propagating to the outside, and a power supply 6 to apply high voltage to the plasma electrode unit 2.

Hereinafter, the respective components 2~6 will be described with reference to the accompanying drawings.

Figure 3:
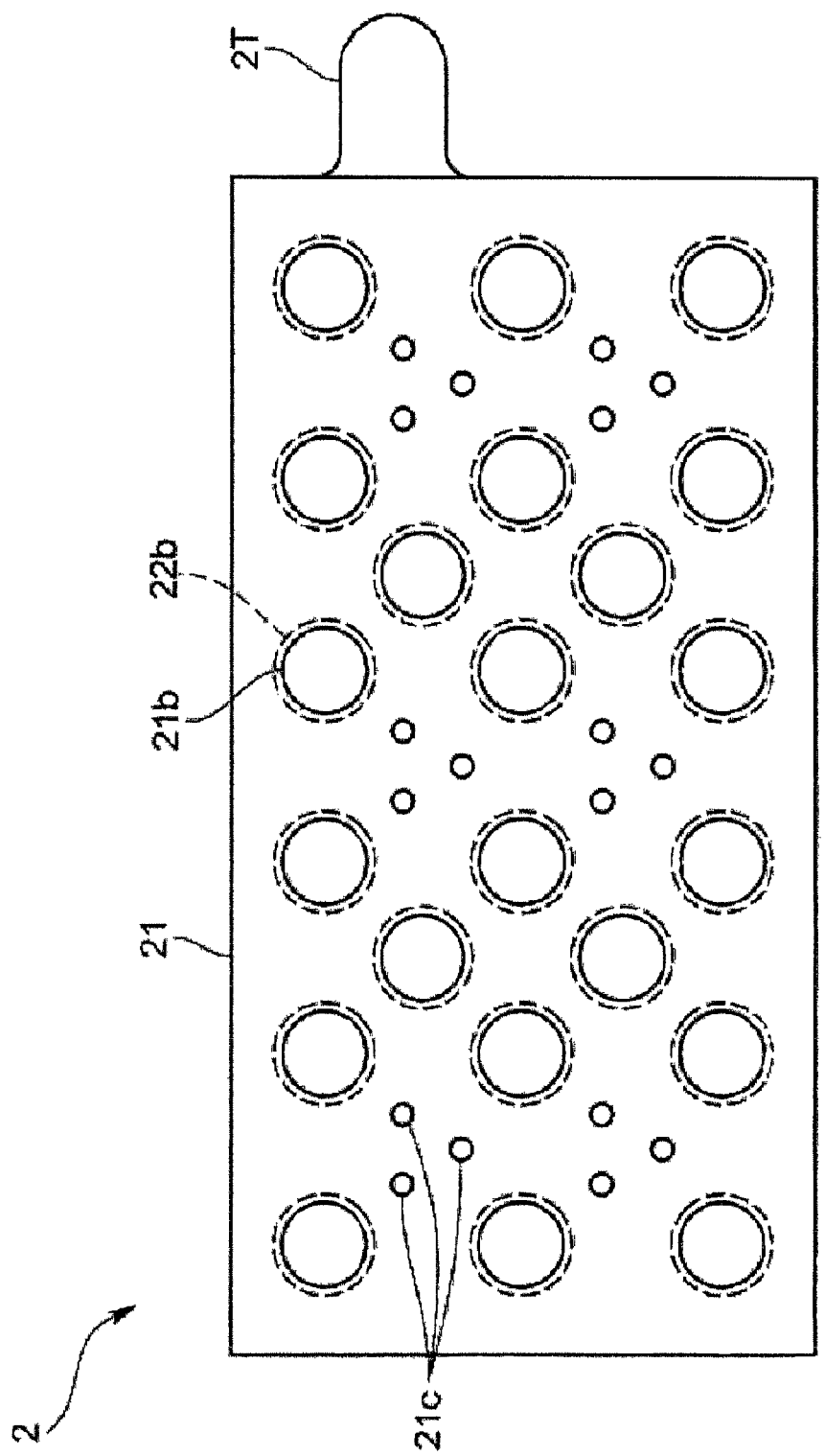
FIG. 3 is a plan view illustrating an electrode unit, according to example embodiments.

The plasma electrode unit 2, as shown in FIGS. 2 to 6B, includes a pair of electrodes 21 and 22 provided with dielectric films 21a and 22a on opposite surfaces thereof, and designated voltage is applied between the electrodes 21 and 22, thereby executing plasma discharge. The respective electrodes 21 and 22, particularly as shown in FIG. 3, have an approximately rectangular shape as seen from the top (the plane direction of the electrodes 21 and 22), and are formed of, for example, stainless steel, such as SUS 403. Application terminals 2T to which voltage from the power supply 6 is applied are formed at the edges of the electrodes 21 and 22 of the electrode unit 2 (with reference to FIG. 3). Here, in a voltage application method of the plasma electrode unit 2 by the power supply 6, voltage in a pulse mode applied to the respective electrodes 21 and 22, a peak value of the voltage is within the range of 100 V to 5,000 V, and a pulse width of the voltage is within the range of 0.1 μs to 300 μs.

Figure 5:
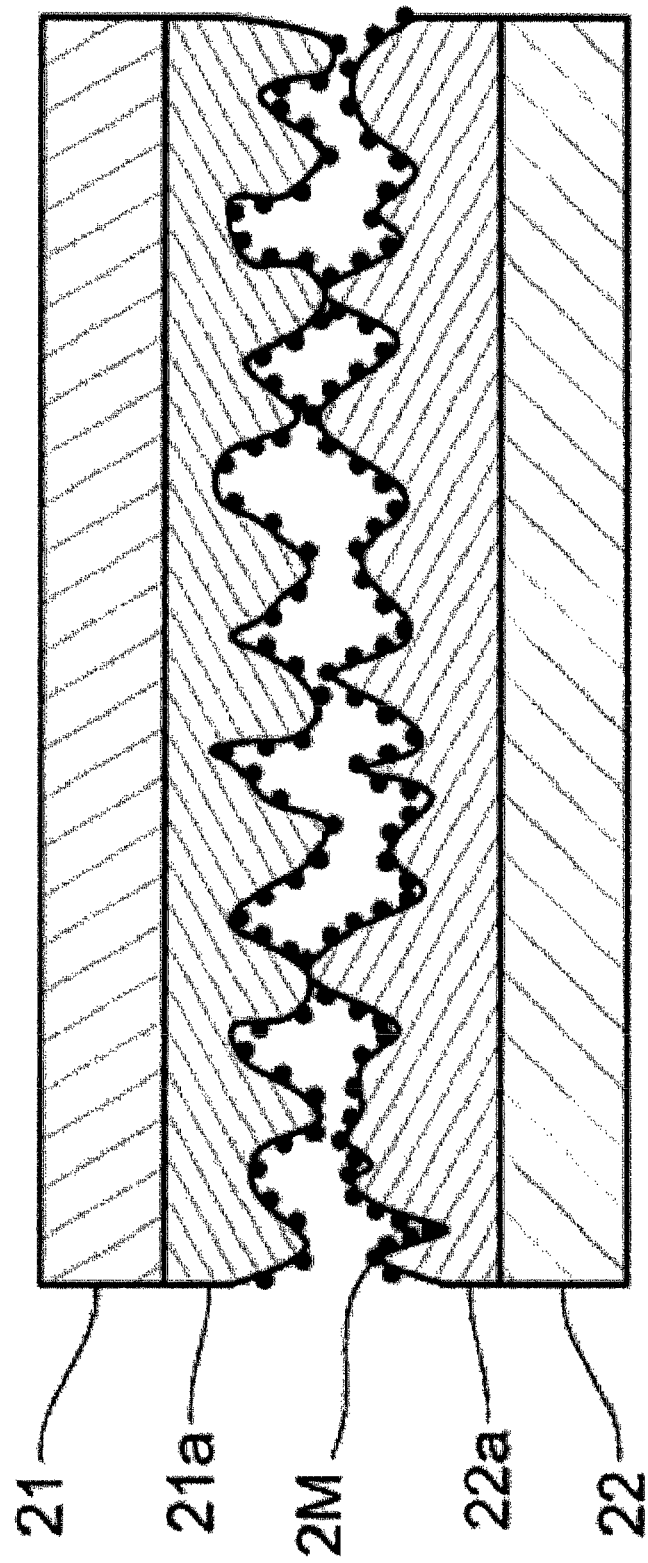
FIG. 5 is an enlarged cross-sectional view illustrating configuration of opposite surfaces of the electrode unit, according to example embodiments.

Further, as shown in FIG. 5, the dielectric films 21a and 22a are formed on the opposite surfaces of the electrodes 21 and 22 by applying a dielectric, for example, barium titanate, to the opposite surfaces of the electrodes 21 and 22. Surface roughness (arithmetic average roughness Ra in this embodiment) of the dielectric films 21a and 22a is more than 0.1 μm and less than approximately 100 μm. Otherwise, maximum height Ry and ten-point average roughness Rz may be used as the surface roughness. By restricting the surface roughness of the dielectric films 21a and 22a to a value within the above range, a gap is formed between the opposite surfaces of the electrodes 21 and 22 only by stacking the electrodes 21 and 22, and plasma is formed within the gap. Thereby, a spacer to form the gap to form plasma is not required between the respective electrodes 21 and 22. Further, control of the surface roughness of the dielectric films 21a and 22a by a thermal spray process is considered. As a non-limiting example, the dielectric applied to the electrodes 21 and 22 may use aluminum oxide, titanium oxide, magnesium oxide, strontium titanate, silicon oxide, silver phosphate, lead zirconate titanate, silicon carbide, indium oxide, cadmium oxide, bismuth oxide, zinc oxide, iron oxide, or carbon nano-tubes.

In order to prevent lowering of performance of the plasma electrode unit 2 due to moisture, a water repellent property is imparted to the opposite surface of at least one of a pair of the electrodes 21 and 22 so that a contact angle of water drops with the opposite surface is more than 90 degrees. In this embodiment, in order to uniformly maintain applied voltage and to keep a large amount of generated active species, even if an excessive amount of moisture contacts the plasma electrode unit 2, the water repellent property is imparted to the opposite surfaces of the electrodes 21 and 22, i.e., the surfaces of the dielectric films 21a and 22a of the electrodes 21 and 22, as shown in FIG. 5. In order to impart the water repellent property, for example, a water repellent thin film 2M formed of a water repellent material is formed by applying a fluorine-based resin mixed solvent to the dielectric films 21a and 22a of the electrodes 21 and 22 to a thin thickness and drying the resin. Such a water repellent thin film 2M is exposed at a plurality of regions on the dielectric films 21a and 22a generating plasma, and repels water without change of a plasma generation state.

Figure 4:
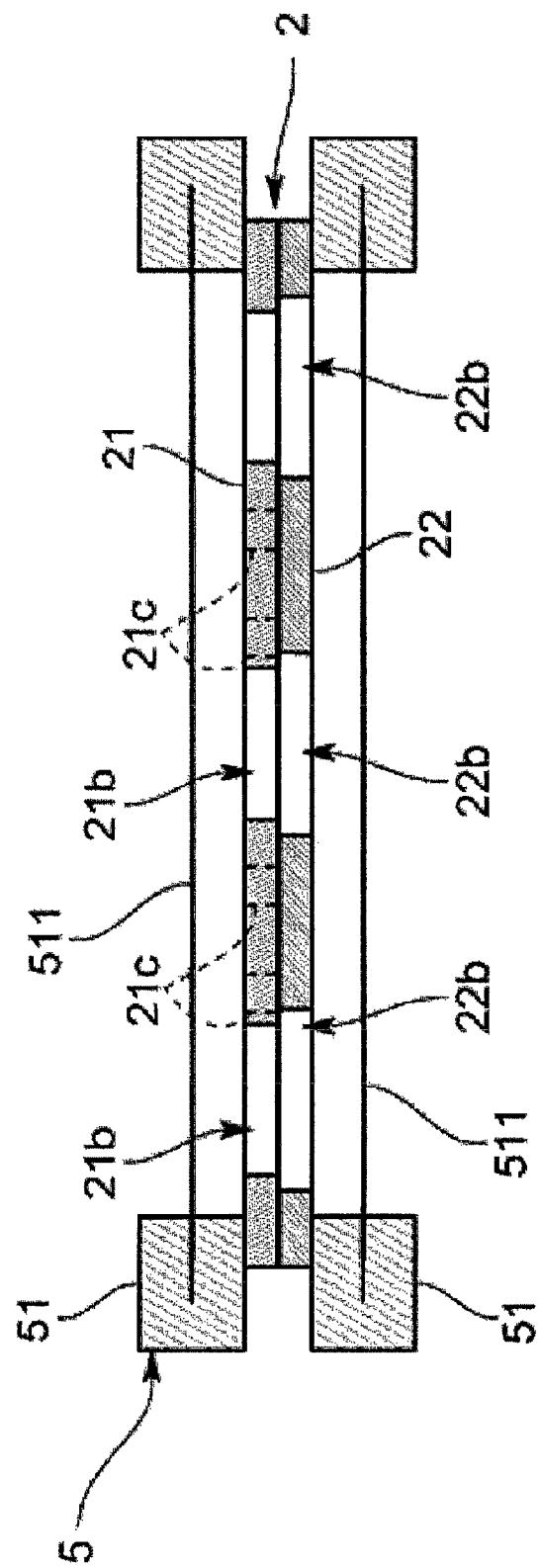
FIG. 4 is a cross-sectional view illustrating the electrode unit and an explosion proof device, according to example embodiments.

Further, as shown in FIGS. 3, 4 and 6, fluid passage holes 21b and 22b are provided at corresponding parts of the respective electrodes 21 and 22 so as to communicate with each other, and are configured such that at least parts of the outlines of the fluid passage holes 21b and 22b are located at different positions as seen from the plane direction of the electrodes 21 and 22 (as seen from the top). That is, the shape of the fluid passage holes 21b formed on one electrode 21 as seen from the top and the shape of the fluid passage holes 22b formed on the other electrode 22 as seen from the top are different.

In more detail, the fluid passage holes 21b and 22b formed at the corresponding parts of the respective electrodes 21 and 22 have an approximately circular shape as seen from the top (with reference to FIGS. 3, 6A and 6B), and an opening size (an opening diameter) of the fluid passage holes 21b formed on the electrode 21 is smaller than an opening size (an opening diameter) of the fluid passage holes 22b formed on the electrode 22 by, for example, 10 μm or more.

Figure 6A:
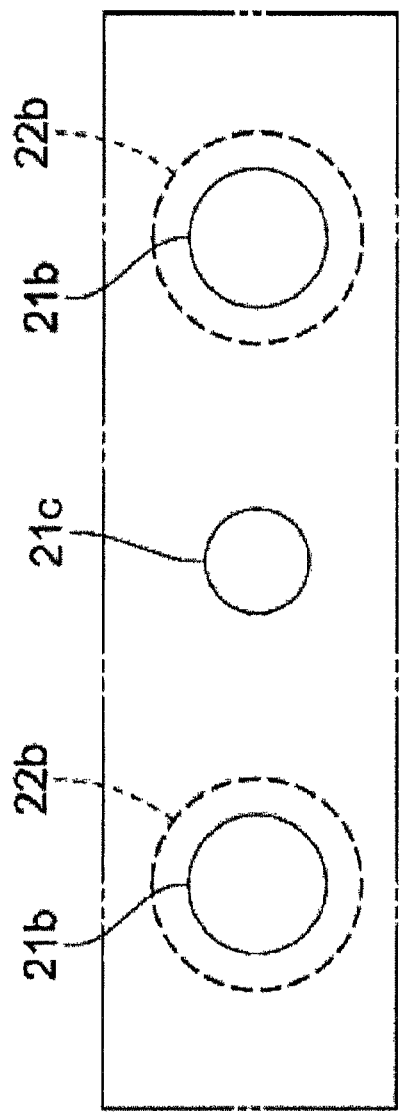
FIGS. 6A and 6B are a partially enlarged plan view and a sectional view schematically illustrating fluid passage holes and through holes, according to example embodiments.
Figure 6B:
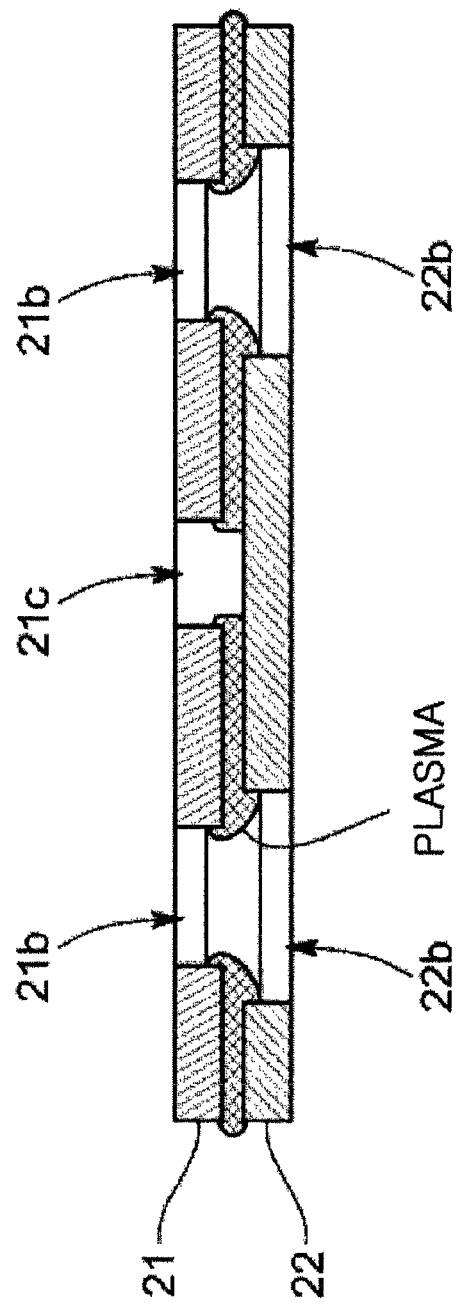

Further, as shown in FIGS. 3, 6A and 6B, the fluid passage holes 21b formed on the electrode 21 and the fluid passage holes 22b formed on the electrode 22 are concentric. Further, in this embodiment, all of the plural fluid passage holes 21b formed on the electrode 21 have the same shape, all of the plural fluid passage holes 22b formed on the electrode 22 have the same shape, and the fluid passage holes 21b formed on the electrode 21 are smaller than the fluid passage holes 22b formed on the electrode 22. Although this embodiment illustrates the fluid passage holes 21b and 22b as having an approximately circular shape, the fluid passage holes 21b and 22b are not limited to the circular shape as long as at least parts of the outlines of the fluid passage holes 21b and 22b are located at different positions as seen from the top.

Further, as shown in FIGS. 3, 6A and 6B, the plasma electrode unit 2 is configured such that through holes 21c are provided on one electrode 21 separately from the fluid passage holes 21b and 22b and openings of the through holes 21c on the opposite surface of the electrode 21 are closed by the other electrode 22. The fluid passage holes 21b and 22b formed on the respective electrodes 21 and 22 are referred to as complete opening parts, and for comparison with the complete opening parts, the through holes 21c are referred to as half opening parts.

An opening size of the through holes 21c is smaller than the opening size of the fluid passage holes 21b by approximately 10 μm or more. The through holes 21c are formed as substitutes for some of the regularly provided fluid passage holes 21b, and are provided around the fluid passage holes 21b (with reference to FIG. 3).

The air blowing device 3 is disposed on the other electrode 22 of the plasma electrode unit 2, and is provided with an air blowing fan which forcibly supplies air toward the fluid passage holes (complete opening parts) 21b and 22b formed on the plasma electrode unit 2. In more detail, a flow velocity of air blown by the air blowing device 3 and passing through the fluid passage holes 21b and 22b is in the range of approximately 0.1 m/s to 10 m/s.

The fine droplet supply device 4 is disposed, for example, on the electrode 22 of the plasma electrode unit 2, as shown in FIGS. 1 and 2. The fine droplet supply device is a mist generator which supplies fine droplets of water having a particle size of approximately 100 μm or less between the plasma electrode unit 2 and the air blowing device 3. That is, the mist generator is disposed to supply fine droplets of water upstream of an air flow from the plasma electrode unit 2. In this case, the reason why the fine droplets of water have a particle size of approximately 100 μm or less is that a distance between the electrodes 21 and 22 is approximately 100 μm or less and steam or fine droplets of water having a particle size of more than approximately 100 μm are excessively large, and thus, do not affect the plasma electrode unit 2. Further, droplets of water having a particle size exceeding approximately 100 μm form, for example, having a water drop shape like rain, are not contained in a fluid and fall by gravity, thus not moving toward the plasma electrode unit 2.

The explosion proof device 5 includes protective covers 51 disposed at the outside of the pair of the electrodes 21 and 22, as shown in FIG. 4, and prevents flame generated from a combustible gas, introduced into the fluid passage holes 21b and 22b, by plasma from propagating to the outside over the protective covers 51. In more detail, each of the protective covers 51 of the explosion proof device 5 includes a metal mesh 511 disposed at the outside of the pair of the electrodes 21 and 22, and the metal mesh 511 has a wire diameter of 1.5 mm or less and an aperture ratio of 30% or more.

Hereinafter, usage of the plasma generation apparatus 100 in accordance with this embodiment will be described. Optimization of the shape of the electrodes to achieve both sterilization and deodorization is achieved by air ion measurement and ozone concentration measurement. These measurements are carried out at positions separated from the plasma electrode unit 2 in the downstream direction by distances at which an air ion counter may be installed. In this embodiment, a suction hole to measure ozone concentration is installed at a position separated from the plasma electrode unit 2 by 1 cm and a suction hole to measure ionized water density is installed at a position separated from the plasma electrode unit 2 by 10 cm. Air ion measurement is an indirect and simple measurement method, and is used to measure ions having charges and a long life from among active species generated from plasma. The air ion measurement uses relations between density of ionized water in air and density of active species under a regular plasma generation condition. That is, a high density of the ionized water means a high density of active species effective in sterilization and deodorization. Since ozone, which is a by-product of plasma, has a much longer life (about 10 minutes or more) than ions, there is little difference between concentration of ozone adjacent to plasma and concentration of ozone at a downstream point separated from the plasma. However, in order to increase the absolute value of a measured value and check small variations of an amount of generated ozone, a sampling suction hole of a measuring instrument is installed at a position separated from the electrode 21 in the downstream direction by 1 cm.

An increase in the amount of generated ions due to the nonsymmetrical structure of electrodes and half opening parts may be confirmed, as below.

Three kinds of electrodes having the same aperture ratio are prepared as in the following:

1) an electrode provided with only symmetrical complete opening parts (i.e., the fluid passage holes 21b and the fluid passage holes 22 having the same shape), 2) an electrode provided with nonsymmetrical complete opening parts, and 3) an electrode provided with half opening parts in addition to symmetrical complete opening parts.

Figure 7:
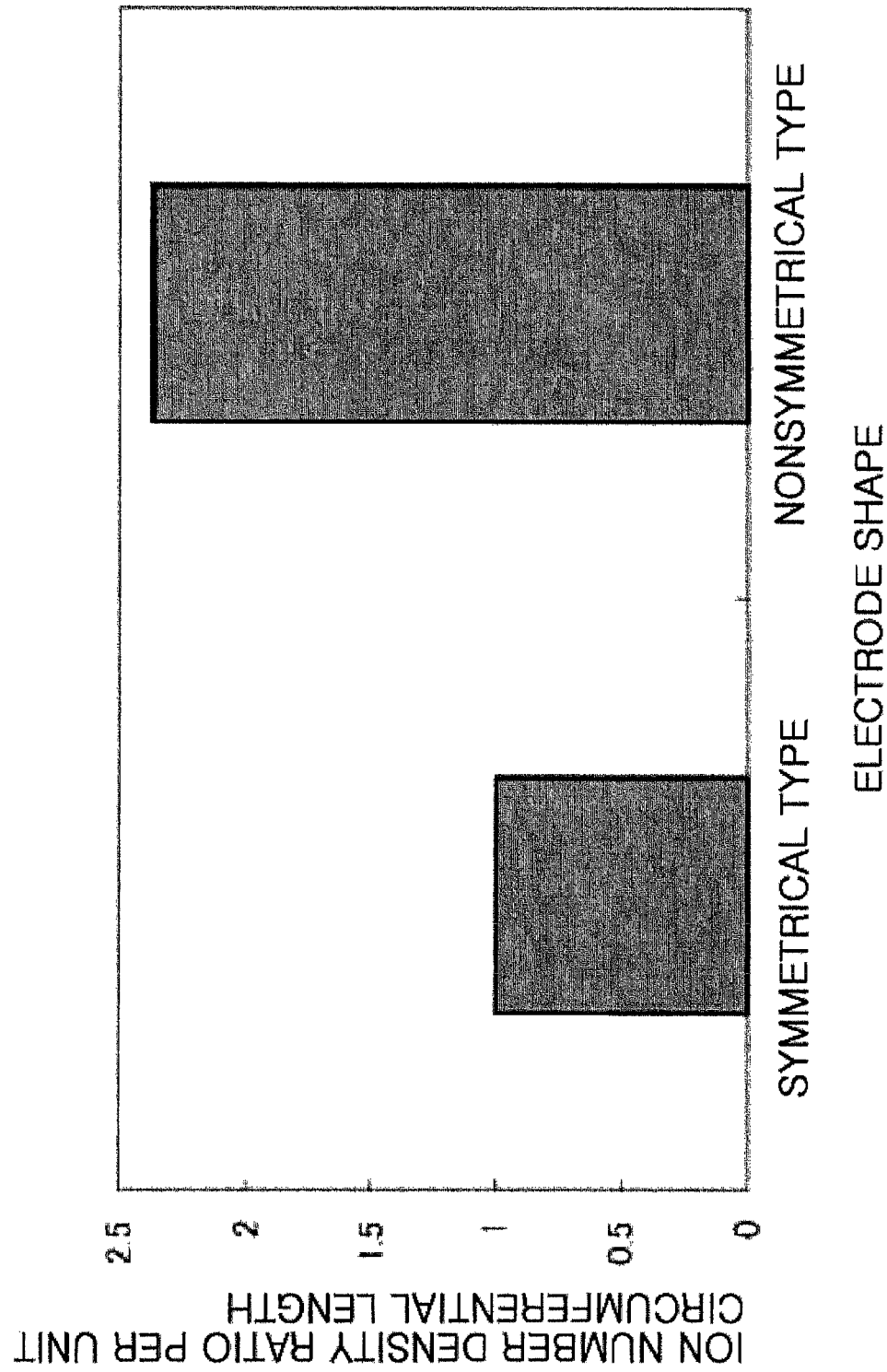
FIG. 7 is a graph illustrating ionized water densities per unit circumferential length (ratios to a symmetrical type) according to electrode shapes, according to example embodiments.
Figure 8:
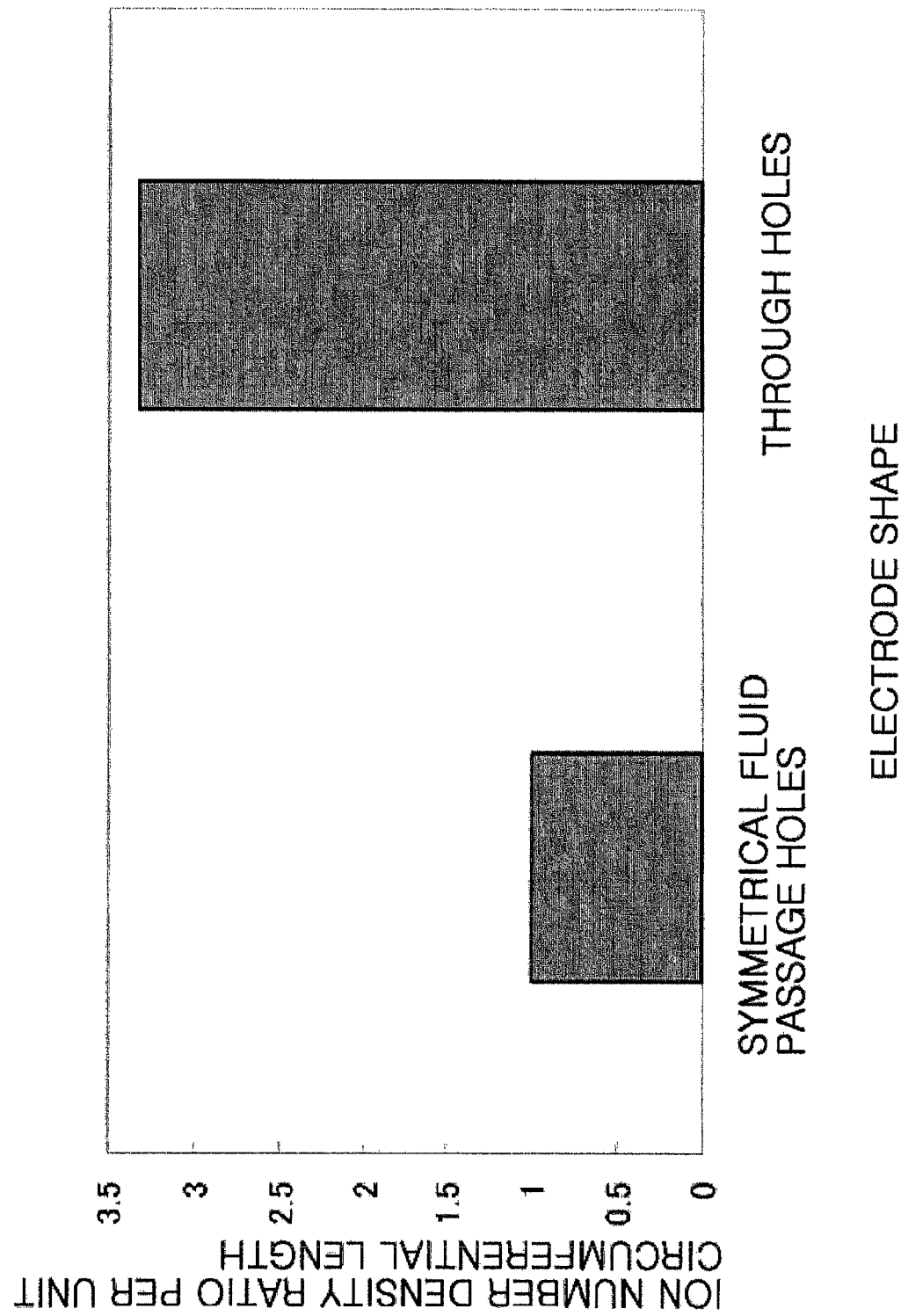
FIG. 8 is a graph illustrating ionized water densities per unit circumferential length (ratios to the symmetrical type) according to the through holes, according to example embodiments.

Voltage applied to the respective electrodes is adjusted to make the concentration of ozone uniform, and densities of ionized water generated under the conditions are measured. Thereafter, the sums of the circumferential lengths of the opening parts of the electrodes are calculated, and ionized water densities per unit circumferential length are calculated by the measured ionized water densities. An increased amount of generated ions due to the nonsymmetrical complete opening parts is obtained by comparing the electrodes 1) and 2) to each other, and an increased amount of generated ions due to the half opening parts is obtained by subtracting the ionized water density of the electrode 1) from the ionized water density of the electrode 3). FIG. 7 is a graph illustrating a ratio of an amount of generated ions of the nonsymmetrical complete opening parts to the symmetrical complete opening parts. As shown in FIG. 7, it is proved that the amount of generated ions of the nonsymmetrical complete opening parts in accordance with this embodiment increases 2 times or more, as compared with the symmetrical complete opening parts. Further, FIG. 8 is a graph illustrating a ratio of an amount of generated ions of the half opening parts to the symmetrical complete opening parts. As shown in FIG. 8, it is proved that the amount of generated ions of the half opening parts in accordance with this embodiment increases 3 times or more, as compared with the symmetrical complete opening parts.

Figure 9:
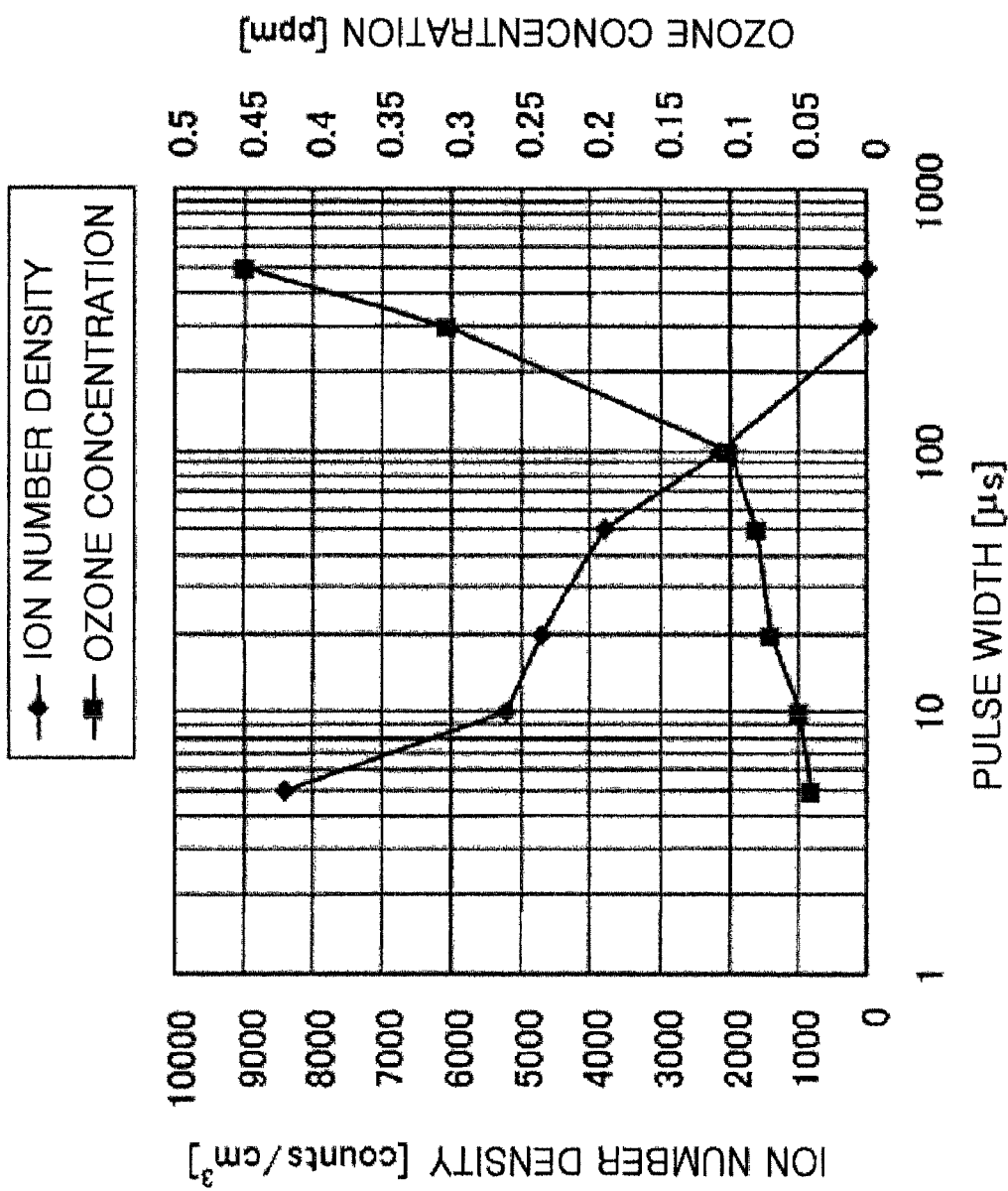
FIG. 9 is a graph illustrating pulse width dependency of ionized water density and ozone concentration, according to example embodiments.

The plasma generation apparatus needs to suppress generation of ozone harmful to human bodies as well as to increase the number of active species contained in a fluid contacting the fluid passage holes. Through the method in accordance with the embodiment, an amount of generated active species may be increased by decreasing a pulse width of a high voltage pulse. Pulse width dependency of ionized water density and ozone concentration shown in FIG. 9 is measured when only a pulse width is changed while allowing a repetition frequency and a peak voltage value of a pulse to be uniformly maintained at 1 k. As shown in FIG. 9, ionized water is measured, an ozone concentration is lowered, and a pulse width is decreased, at a pulse width of approximately 100 μs or less, and thus the ionized water is increased and the ozone concentration is decreased. Consequently, the ozone concentration may be suppressed to a low concentration and the ionized water density may be increased. Therefore, it is understood that the pulse width is approximately 100 μs or less.

Figure 10:
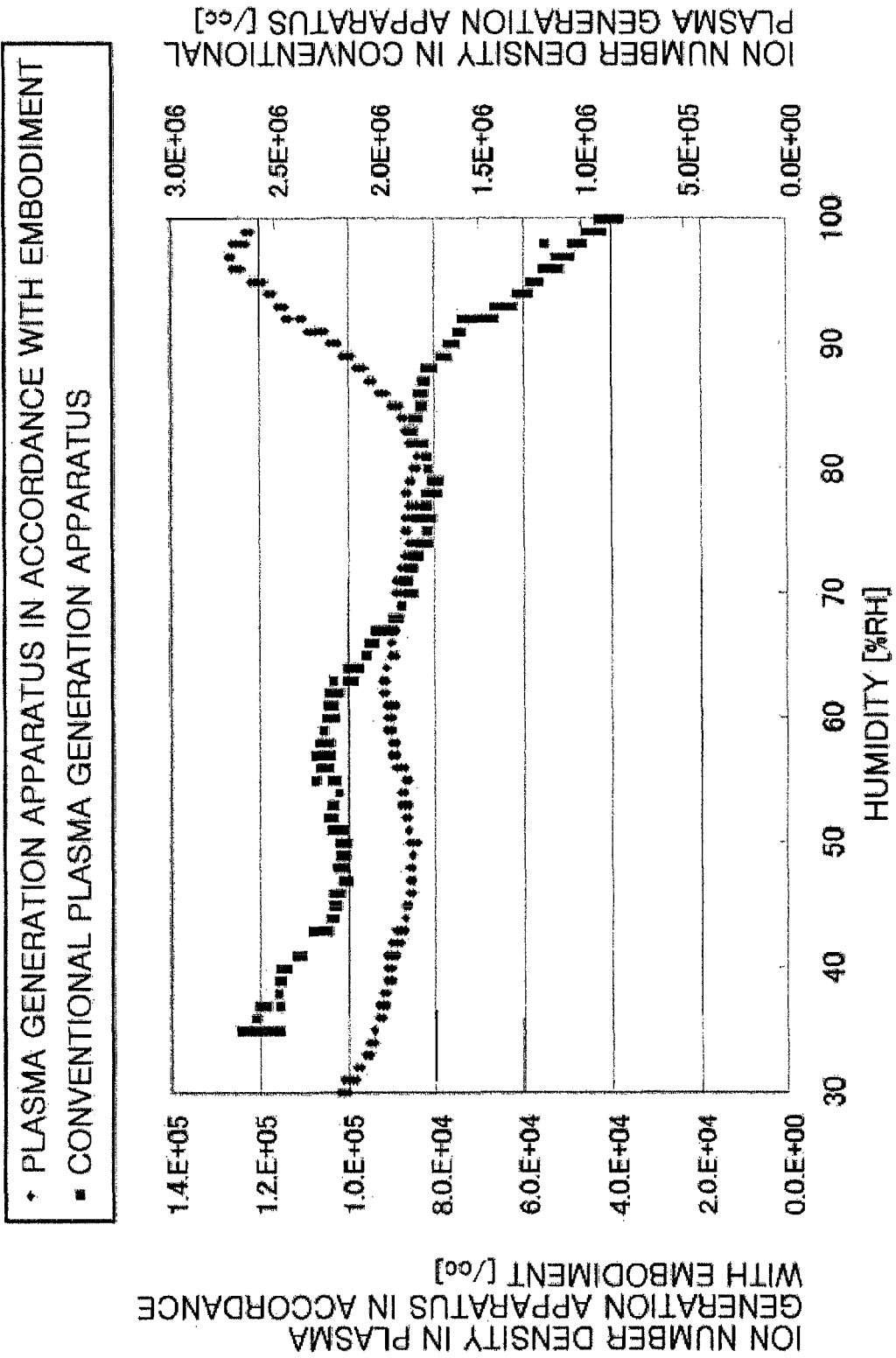
FIG. 10 is a graph illustrating relations between relative humidity and ionized water density, according to example embodiments.

Performance evaluation of the plasma generation apparatus in accordance with this embodiment and the conventional plasma generation apparatus is executed through measurement of air ions in a high humidity condition. FIG. 10 is a graph illustrating results of measurement of ionized water densities when relative humidity is changed. From FIG. 10, in the case of the plasma generation apparatus in accordance with this embodiment, it is understood that the ionized water density is decreased around a humidity of approximately 75% RH, and is rapidly increased at a high humidity of approximately 90~100% RH, and a density of generated active species is high in the high humidity condition. On the other hand, in the case of the conventional plasma generation apparatus, the ionized water density is decreased in proportion to increase of humidity, and is rapidly decreased at a high humidity of approximately 90~100% RH. Further, the plasma generation apparatus in accordance with this embodiment and the conventional plasma generation apparatus have different ionized water density ranges because the plasma generation apparatus in accordance with this embodiment and the conventional plasma generation apparatus have different sizes of main bodies, or generate different active species.

Further, a sterilization test of colon bacilli is carried out using the plasma generation apparatus in accordance with this embodiment. As a result of operation of the plasma generation apparatus in a chamber having a volume of approximately 100 L for 6 hours under the condition that a laboratory dish inserted into an agar medium containing colon bacilli is placed in the chamber and humidity is maintained at approximately 90% RH, colonies derived from bacilli are reduced and may be sterilized, as shown in photographs of FIG. 11. Since colon bacilli are suppressed in the humidity condition having a small number of ions, as described above, it is understood that colon bacilli may also be sterilized in the high humidity area having a large number of ions.

Figure 12:
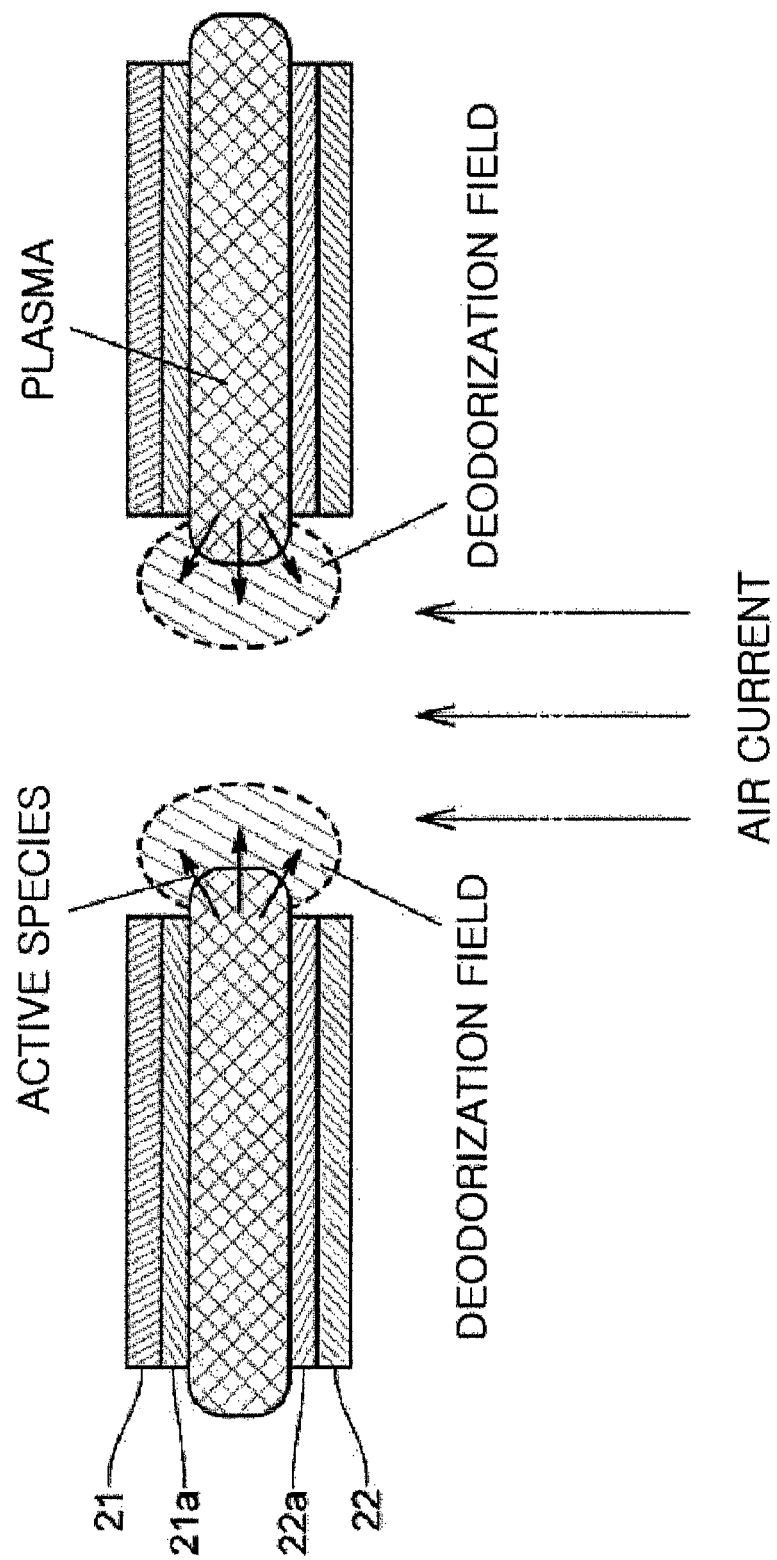
FIG. 12 is a sectional view illustrating plasma generation and deodorization fields, according to example embodiments.

Deodorization executed around electrodes will be described, as below. First, a difference between concentration of active species generated by plasma and concentration of odors conveyed by an air current is considered. As shown in FIG. 12, a portion of plasma generated in a gap between the respective dielectric films $21a$ and $22a$ on the surfaces of the electrodes 21 and 22 is diffused into the fluid passage holes, and thus the generated active species interact with the air current supplied from the air blowing device. Since an electron density of plasma generated from a space interposed between the dielectric films $21a$ and $22a$ at the atmospheric pressure is about $1015/cm^3$ and a density of generated ions or radicals is the same as the electron density, active species of a considerably high density are present. Further, a molecular number density supposed when molecules of an odor material are conveyed is approximately $1013/cm^3$ even in units of ppm, and has a smaller number of ciphers than the density of the active species. That is, a space, in which a number of active species sufficient to decompose odor molecules are generated, is formed within the fluid passage hole, and research into methods of transferring the active species to deodorization fields, as shown in FIG. 12, to promote decomposition of the odor molecules is crucial. From among the methods, there is a method in which forced air is transferred to the fluid passage hole. Odor molecules contact the fluid passage hole provided with the deodorization fields by forcibly transferring the air to the fluid passage hole, thus being decomposed. There is another method in which odor molecules are transferred to the fluid passage hole by forced air generated by rotating a cylindrical member at a position adjacent to the front surfaces of electrodes at a high speed, and are then decomposed in the deodorization fields.

Figure 13:
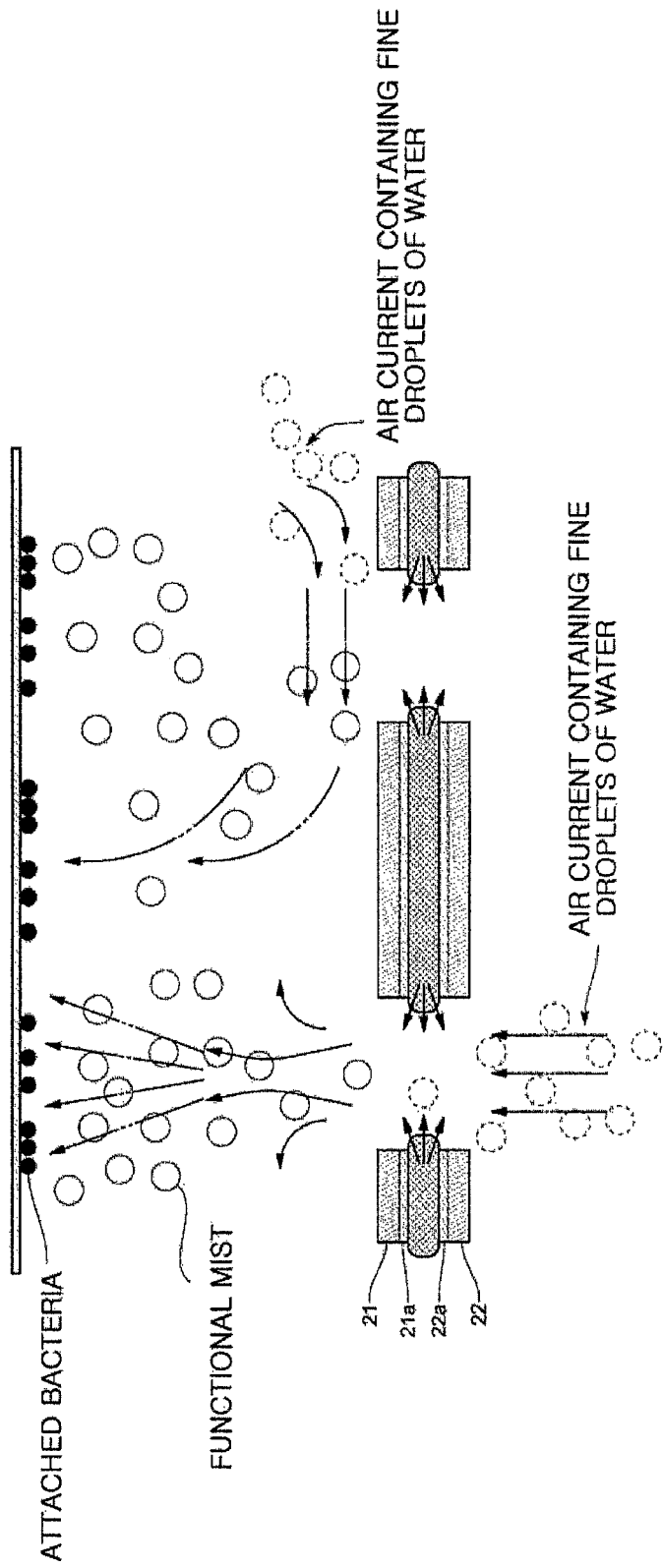
FIG. 13 is a schematic view illustrating sterilization by discharged active species and functional mist, according to example embodiments.

Next, sterilization executed on the surface of an object separated from the electrodes will be described. Sterilization efficiency is determined by a difference between a density of discharged active species and a density of attached bacteria. As shown in FIG. 13, active species are generated by plasma charge, or are mixed with steam or fine droplets of water contained in an air current, are discharged to the outside of the apparatus as functional mist, and are then returned to stable molecules via recombination, etc., according to lives of the respective active species. In general, such ions present in air are measured by an air ion measuring instrument, and have a density of about $106/cm^3$ around plasma. When the active species, as functional mist, are diffused at such a low number density, a long time is required to decompose odor molecules, and thus, deodorizing effects are not expected, but the active species are effective in sterilization of attached bacteria having a lower number density. There are hundreds to thousands of attached bacteria per unit area, i.e., approximately $102\sim103/cm^2$, and the attached bacteria continuously contact the active species in the functional mist for a designated time, and are thus sterilized.

Figure 14:
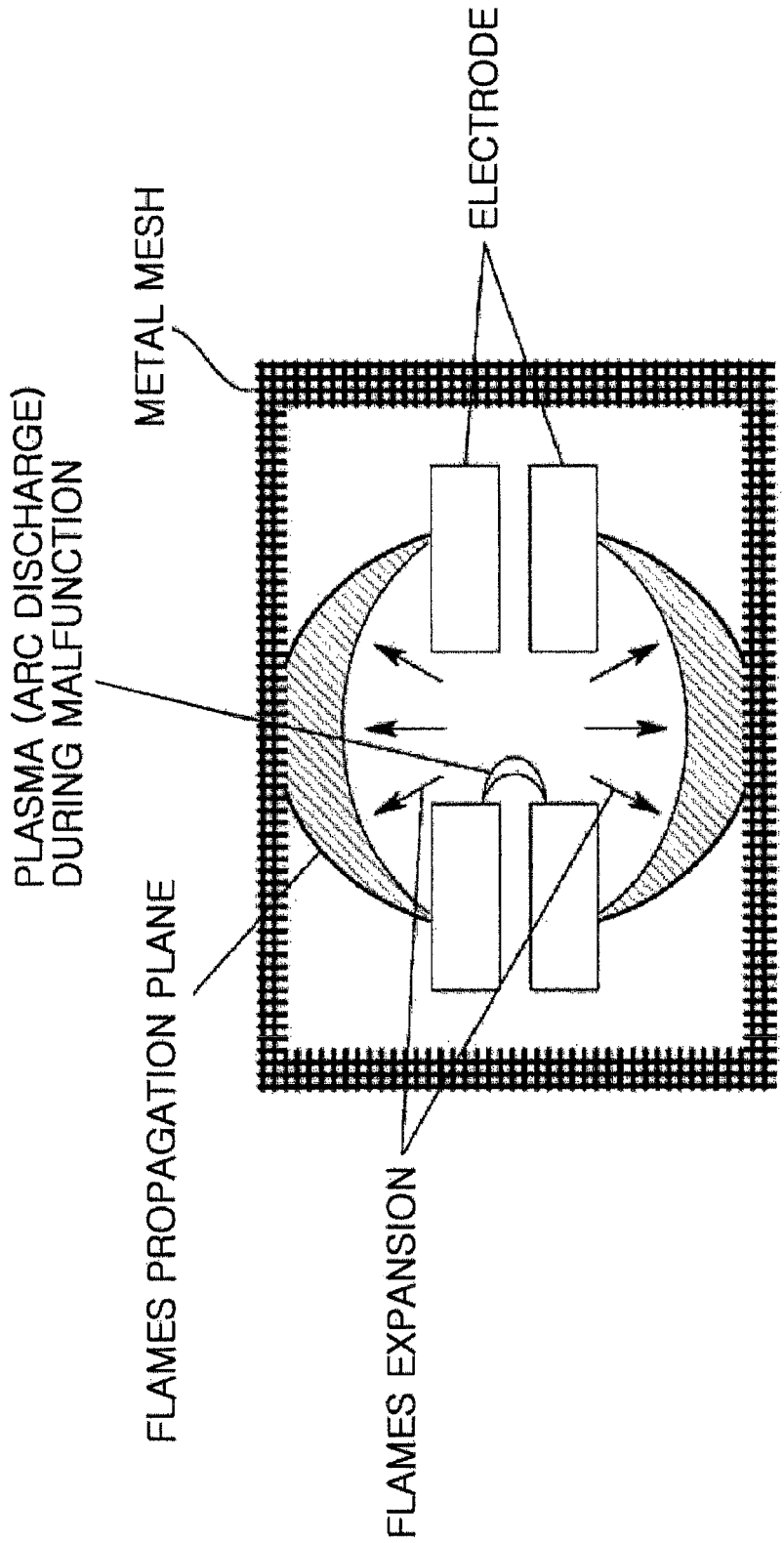
FIG. 14 is a schematic view illustrating ignition by plasma and prevention of flame propagation by an explosion proof device during malfunction, according to example embodiments.
Figure 15:
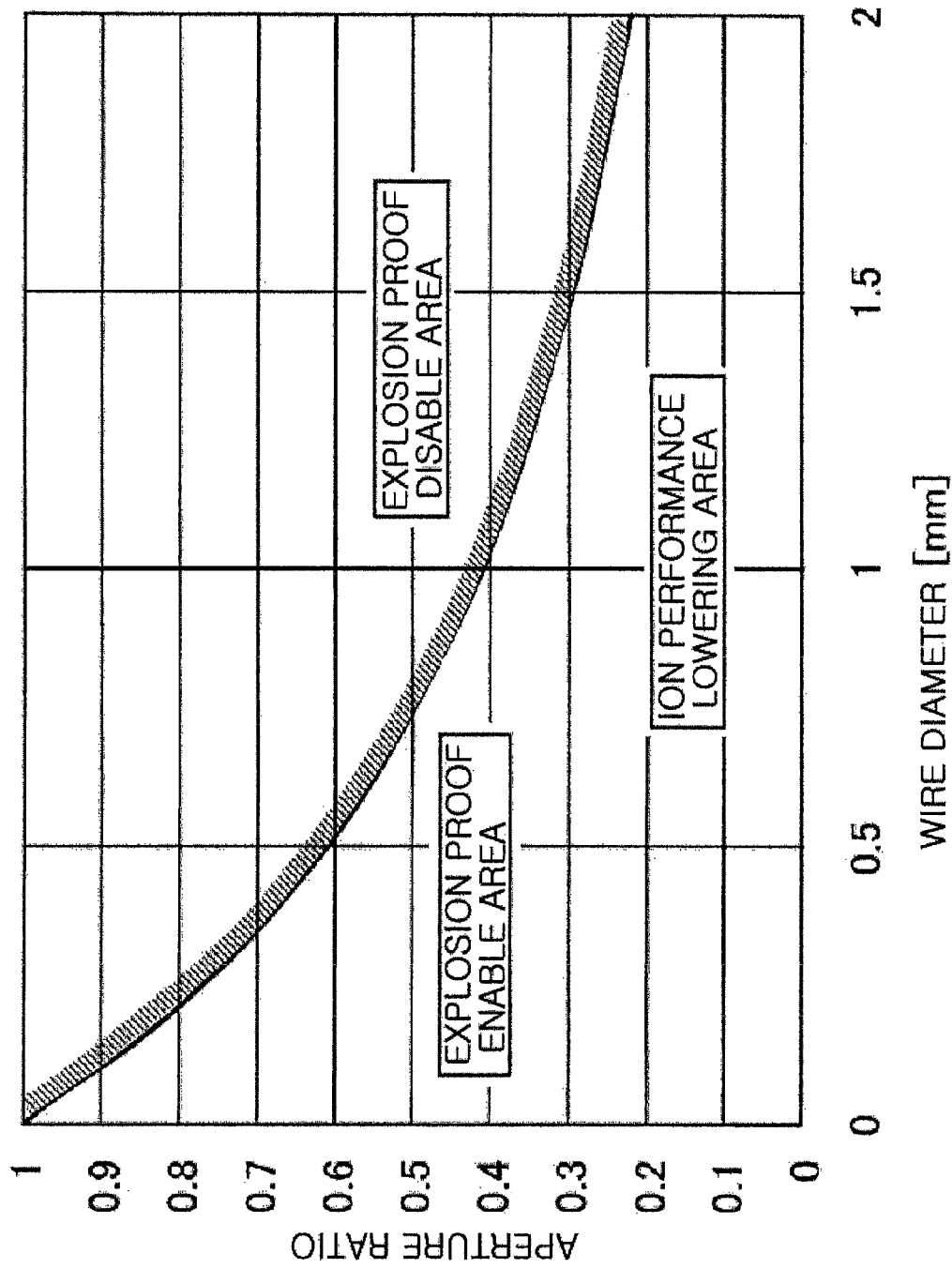
FIG. 15 is a view illustrating a parameter region of a metal mesh satisfying an explosion proof capacity and ion discharge performance, according to example embodiments.

The explosion proof device 5 is required, for example, if the apparatus in accordance with this embodiment is installed in a refrigerator using a combustible refrigerant. As shown in FIG. 14, even if the metal meshes 511 are disposed around the plasma electrode unit 2 and a spark, such as arc discharge, is generated on the electrodes and ignites in a combustible refrigerant atmosphere, flame is not diffused to the entirety of the refrigerator over the metal meshes 511. Particularly, as shown in FIG. 15, when the metal meshes 511 have a wire diameter of approximately 1.5 mm or less or an aperture ratio of approximately 30% or more, the apparatus may be operated without loss of the amount of generated active species increased due to the above electrode structure, i.e., may obtain safety without lowering deodorizing and sterilizing capacities.

In the above-described plasma generation apparatus 100 in accordance with this embodiment, a contact area between plasma generated from the respective corresponding fluid passage holes and a fluid is increased, thereby increasing an amount of generated active species. Further, steam or fine droplets of water contact the active species generated from the fluid passage holes, and thus the active species charge or are mixed with the steam or fine droplets of water, become functional mist, and are then discharged to the outside, thereby sterilizing flowing bacteria and attached bacteria. Moreover, the amount of the active species generated from plasma is increased, thereby exhibiting a sufficient deodorizing function.

The disclosure is not limited to the above embodiment of the present disclosure.

As a non-limiting example, although the above embodiment illustrates the fine droplet supply device, a steam supply device may be provided. In this case, as the steam supply device, a steam generator may be installed instead of the mist generator. Further, the steam supply device may include a water supply unit to supply water to at least one electrode among a pair of electrodes to attach moisture to the electrode, and a heating unit to evaporate the moisture attached to the electrode. In this case, as the heating unit, a heater may be provided separately from the electrodes, or heat generated during generation of plasma from the electrode unit may be used. Further, both the steam supply device and the fine droplet supply device may be provided.

Figure 16:
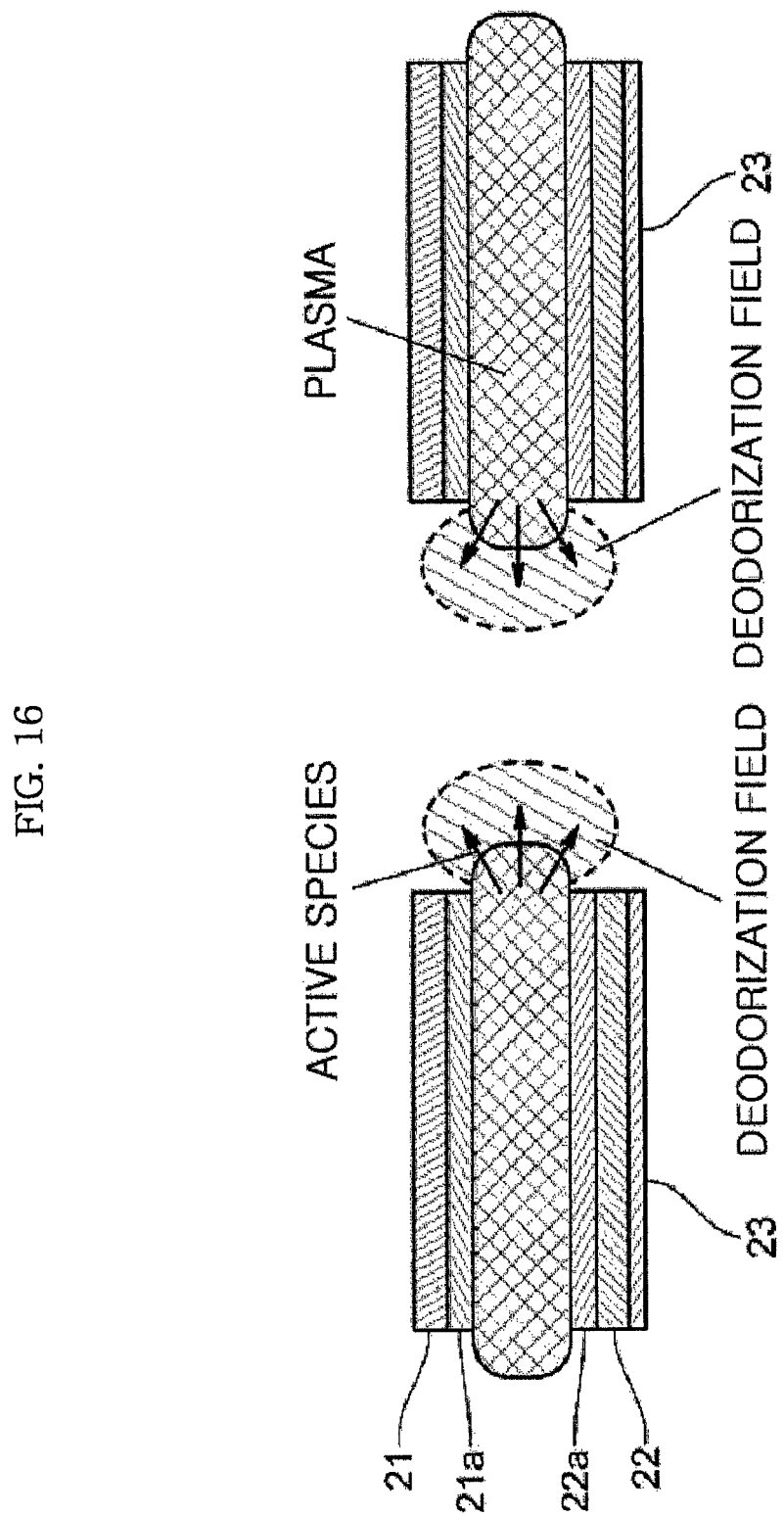
FIG. 16 is a sectional view illustrating configuration of an electrode unit with a heating unit, according to example embodiments.

As shown in FIG. 16, a heating unit 23 is provided on at least one electrode among a pair of electrodes and heats the electrodes to evaporate moisture and dry the electrodes. In this case, an electric heating wire, such as a heating resistor provided on the surface of the at least one electrode opposite to the opposite surface, may be used as the heating unit 23, as shown in FIG. 16. Thereby, evaporated moisture may become steam or fine droplets of water and be used as a raw material of functional mist as well as an area in which plasma is generated may be maximized and a large amount of generated active species may be maintained.

Further, a temperature sensor may be provided on at least one electrode among a pair of electrodes such that steam or fine droplets of water are supplied when a temperature detected by the temperature sensor is more than a designated value. In this case, a control device acquires a detection signal from the temperature sensor and compares a temperature indicated by the detection signal with a predetermined value, simultaneously, and outputs a mist generation signal to the mist generator upon judging that the temperature of the electrodes is more than the designated value. Then, the mist generator acquires the mist generation signal and supplies mist toward the plasma electrode unit. In addition, the control device may be configured to execute feedback control of an amount of supplied mist or steam based on the temperature of the electrodes.

Further, if the temperature sensor to measure the temperature of at least one electrode, among a pair of electrodes, and the heating unit to heat at least one electrode, among the pair of electrodes, may be provided, the heating unit may be configured to heat the electrodes if the temperature detected by the temperature sensor is less than a designated value. Further, the control device acquires a detection signal from the temperature sensor and compares a temperature indicated by the detection signal with a predetermined value, simultaneously, and supplies current to the heating unit, i.e., the heating resistor, upon judging that the temperature of the electrodes is less than the designated value. Thereby, the electrode unit is heated to evaporate water drops attached to the electrode unit, and functional mist is generated using generated steam. In addition, the control device may be configured to execute feedback control of a heating temperature of the heating unit based on the temperature of the electrodes.

Further, a humidity sensor to measure a relative humidity in the atmosphere between a pair of electrodes may be provided to supply steam or fine droplets of water when the humidity detected by the humidity sensor is less than a designated value. In this case, the control device acquires a detection signal from the humidity sensor and compares a humidity indicated by the detection signal with a predetermined value, simultaneously, and outputs a mist generation signal to the mist generator upon judging that the relative humidity in the atmosphere is less than the designated value (for example, approximately 90% RH). Then, the mist generator acquires the mist generation signal and supplies mist toward the plasma electrode unit. In addition, the control device may be configured to execute feedback control of an amount of supplied mist or steam based on the relative humidity.

Although this embodiment illustrates the plural fluid passage holes 21b of the electrode 21 as having the same shape and the plural fluid passage holes 22b of the electrode 22 as having the same shape, the plural fluid passage holes 21b and the plural fluid passage holes 22b may have different shapes.

Further, although this embodiment illustrates all of the fluid passage holes 21b of the electrode 21 as being larger or smaller than all of the fluid passage holes 22b of the electrode 22, some of the fluid passage holes 21b of the electrode 21 may be smaller than the fluid passage holes 22b of the electrode 22 and the remaining fluid passage holes 21b may be larger than the fluid passage holes 22b of the electrode 22.

Further, although this embodiment illustrates the through holes as being formed on either of the electrodes 21 and 22, the through holes (half opening parts) may be formed on both the electrodes 21 and 22.

Further, although this embodiment illustrates the fluid passage holes 21b and 22b as having cross-sections having designated diameters, the fluid passage holes 21b and 22b formed on the respective electrodes 21 and 22 may have various shapes, such as a shape having a tapered plane, a mortar shape or a bowl shape, i.e., a shape having a diameter decreased or increased from one opening to the other opening.

Further, the fluid passage holes 21b and 22b may have various shapes other than a circle, i.e., an oval, a rectangle, a rectilinear slit, a concentric slit, a wave-shaped slit, a crescent moon, a comb, a honeycomb, or a star.

As is apparent from the above description, a plasma generation apparatus and method in accordance with example embodiments of the present disclosure achieve both sterilization and deodorization of attached bacteria even under the condition that steam or fine droplets of water are present.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A plasma generation method, the method comprising:
preparing a pair of electrodes; and
applying a designated voltage between the pair of electrodes to carry out plasma discharge,
wherein fluid passage holes are provided at corresponding parts of respective electrodes so as to communicate with each other, and steam or fine droplets of water are applied to the fluid passage holes and plasma generated around the fluid passage holes.

2. The plasma generation method of claim 1, wherein the fluid passage holes of each respective electrode, among the pair of electrodes, are concentric with the fluid passage holes of the other electrode.

3. A plasma generation method, the method comprising:
preparing a pair of electrodes; and
applying a designated voltage between the pair of electrodes,
wherein through holes are provided on one electrode such that openings of the through holes on an opposite surface of the electrode facing the other electrode is closed by the other electrode, and steam or fine droplets of water are applied to openings of the through holes on the other surface of the electrode and plasma generated around the through holes.

4. The plasma generation method of claim 3, wherein the fine droplets of water have a particle size of 100 μm or less.

5. The plasma generation method of claim 4, wherein voltage in a pulse mode is applied to each respective electrode and has a peak value within a range of 100V to 5,000V and a pulse width within a range of 0.1 μs to 300 μs.

6. The plasma generation method of claim 5, wherein the steam or fine droplets of water are supplied when a temperature of the pair of electrodes is more than a designated value.

7. The plasma generation method of claim 6, wherein the pair of electrodes is heated by a heating unit when the temperature of the pair of electrodes is less than the designated value.

* * * * *